(12) United States Patent
Bell et al.

(10) Patent No.: US 9,439,746 B2
(45) Date of Patent: Sep. 13, 2016

(54) METHODS AND APPARATUS FOR TREATING VENTRAL WALL HERNIA

(75) Inventors: Stephen G. Bell, Rome (IT); Wayne A. Noda, Mission Viejo, CA (US); Giuseppe Amato, Palermo (IT)

(73) Assignee: Insightra Medical, Inc., Irvine, CA (US)

( * ) Notice: Subject to any disclaimer, the term of this patent is extended or adjusted under 35 U.S.C. 154(b) by 1704 days.

(21) Appl. No.: 12/183,930

(22) Filed: Jul. 31, 2008

(65) Prior Publication Data

US 2009/0216253 A1    Aug. 27, 2009

Related U.S. Application Data

(60) Provisional application No. 60/013,619, filed on Dec. 13, 2007, provisional application No. 61/030,439, filed on Feb. 21, 2008.

(51) Int. Cl.
| | |
|---|---|
| *A61B 17/10* | (2006.01) |
| *A61F 2/00* | (2006.01) |
| *A61B 17/02* | (2006.01) |
| *A61B 17/06* | (2006.01) |
| *A61B 17/062* | (2006.01) |
| *A61B 17/34* | (2006.01) |
| *A61B 17/00* | (2006.01) |

(52) U.S. Cl.
CPC .......... *A61F 2/0045* (2013.01); *A61B 17/0293* (2013.01); *A61B 17/0625* (2013.01); *A61B 17/06066* (2013.01); *A61B 17/3423* (2013.01); *A61B 2017/003* (2013.01); *A61B 2017/00438* (2013.01); *A61B 2017/00477* (2013.01); *A61B 2017/00805* (2013.01)

(58) Field of Classification Search
USPC .............. 600/29–30, 37; 606/144, 148, 151; 623/23.72
See application file for complete search history.

(56) References Cited

U.S. PATENT DOCUMENTS

| | | | | |
|---|---|---|---|---|
| 2,738,790 | A * | 3/1956 | Todt, Sr. et al. | 606/145 |
| 4,188,945 | A * | 2/1980 | Wenander | 128/850 |
| 5,219,358 | A | 6/1993 | Bendel et al. | |
| 5,337,736 | A * | 8/1994 | Reddy | 600/217 |
| 5,431,323 | A | 7/1995 | Smith et al. | |
| 5,458,609 | A | 10/1995 | Gordon et al. | |
| 5,640,977 | A * | 6/1997 | Leahy et al. | 128/897 |

(Continued)

FOREIGN PATENT DOCUMENTS

| | | |
|---|---|---|
| WO | 9800069 | 1/1998 |
| WO | 03096929 | 11/2003 |

(Continued)

OTHER PUBLICATIONS

Stephen Graham Bell, Wayne A. Noda, Giuseppe Amato "Implant for Hernia Repair" file history of related U.S. Appl. No. 13/476,202, filed May 21, 2002.

(Continued)

*Primary Examiner* — Melanie Tyson
(74) *Attorney, Agent, or Firm* — John L. Rogitz

(57) ABSTRACT

This invention relates to a surgical implant system for repairing abdominal hernias and is particularly useful for repairing ventral hernias. In particular, the present invention relates to an implant, a delivery device and a method for implanting the implant. The implant is implanted in a substantially slackened condition relative to the ventral wall.

8 Claims, 14 Drawing Sheets

(56) References Cited

U.S. PATENT DOCUMENTS

| | | | |
|---|---|---|---|
| 5,716,367 A * | 2/1998 | Koike et al. | 606/144 |
| 5,810,721 A * | 9/1998 | Mueller et al. | 600/206 |
| 5,899,909 A * | 5/1999 | Claren et al. | 606/119 |
| 5,972,022 A | 10/1999 | Huxel | |
| 6,332,888 B1 | 12/2001 | Levy et al. | |
| 6,382,214 B1 | 5/2002 | Raz et al. | |
| 6,383,201 B1 | 5/2002 | Dong | |
| 6,451,032 B1 | 9/2002 | Ory et al. | |
| 6,475,135 B1 | 11/2002 | Levy | |
| 6,911,003 B2 | 6/2005 | Anderson et al. | |
| 6,936,054 B2 | 8/2005 | Chu | |
| 6,984,237 B2 | 1/2006 | Hatch et al. | |
| 6,991,637 B2 | 1/2006 | Crawley et al. | |
| 7,101,381 B2 | 9/2006 | Ford et al. | |
| 7,131,943 B2 | 11/2006 | Kammerer | |
| 7,229,453 B2 | 6/2007 | Anderson et al. | |
| 7,338,502 B2 | 3/2008 | Rosenblatt | |
| 7,404,819 B1 | 7/2008 | Darios et al. | |
| 7,785,334 B2 | 8/2010 | Ford et al. | |
| 2002/0103494 A1 | 8/2002 | Pacey | |
| 2003/0176762 A1* | 9/2003 | Kammerer | 600/30 |
| 2003/0192553 A1* | 10/2003 | Rambo | 128/850 |
| 2004/0015155 A1 | 1/2004 | Whalen et al. | |
| 2004/0039453 A1* | 2/2004 | Anderson et al. | 623/23.72 |
| 2004/0054353 A1 | 3/2004 | Taylor | |
| 2004/0068159 A1* | 4/2004 | Neisz et al. | 600/29 |
| 2004/0144395 A1 | 7/2004 | Evans et al. | |
| 2004/0221431 A1 | 11/2004 | Wittmann | |
| 2005/0004576 A1* | 1/2005 | Benderev | 606/72 |
| 2005/0250977 A1* | 11/2005 | Montpetit et al. | 600/29 |
| 2006/0058575 A1 | 3/2006 | Zadden et al. | |
| 2006/0083767 A1* | 4/2006 | Deusch et al. | 424/422 |
| 2006/0205995 A1 | 9/2006 | Browning | |
| 2006/0258898 A1 | 11/2006 | Montpetit et al. | |
| 2006/0276908 A1 | 12/2006 | Sogaard-Andersen et al. | |
| 2006/0282105 A1 | 12/2006 | Ford et al. | |
| 2007/0239208 A1 | 10/2007 | Crawford | |
| 2007/0260179 A1 | 11/2007 | Sholev et al. | |
| 2007/0270890 A1 | 11/2007 | Miller | |
| 2008/0065229 A1 | 3/2008 | Adams | |
| 2008/0081945 A1 | 4/2008 | Toso et al. | |
| 2008/0109015 A1 | 5/2008 | Chu et al. | |
| 2008/0132753 A1* | 6/2008 | Goddard | 600/37 |
| 2008/0147200 A1 | 6/2008 | Rousseau et al. | |
| 2008/0200751 A1 | 8/2008 | Browning | |
| 2008/0269896 A1 | 10/2008 | Cherok et al. | |
| 2009/0171142 A1 | 7/2009 | Chu | |
| 2009/0192530 A1 | 7/2009 | Azdich et al. | |
| 2009/0198260 A1 | 8/2009 | Ford et al. | |
| 2009/0216253 A1 | 8/2009 | Bell et al. | |
| 2009/0240267 A1 | 9/2009 | Crawley et al. | |
| 2011/0130774 A1 | 6/2011 | Criscuolo et al. | |
| 2011/0184429 A1 | 7/2011 | Saldinger | |
| 2011/0295283 A1 | 12/2011 | Darois et al. | |

FOREIGN PATENT DOCUMENTS

| | | |
|---|---|---|
| WO | 2004012579 | 2/2004 |
| WO | 2005110274 A2 | 11/2005 |
| WO | 2006108145 | 10/2006 |
| WO | 2007016698 | 2/2007 |
| WO | 2007109508 | 9/2007 |
| WO | 2007149348 | 12/2007 |
| WO | 2010039249 A1 | 4/2010 |
| WO | 2010141321 A1 | 12/2010 |

OTHER PUBLICATIONS

Stephen Graham Bell, Giuseppe Amato, "Implant for Hernia Repair", related U.S. Appl. No. 13/443,266, final office action dated Jun. 6, 2013.

Stephen Graham Bell, Giuseppe Amato, "Implant for Hernia Repair", related U.S. Appl. No. 13/443,266, applicants response to final office action filed Jul. 9, 2013.

Stephen Graham Bell, Wayne A. Noda, Giuseppe Amato, "Implant for Hernia Repair" non-final office action dated Apr. 22, 2014 from co-pending U.S. Appl. No. 13/476,202.

Stephen Graham Bell, Wayne A. Noda, Giuseppe Amato, "Implant for Hernia Repair" response to non-final office action filed May 22, 2014 from co-pending U.S. Appl. No. 13/476,202.

Stephen Graham Bell, Giuseppe Amato, "Implant for Hernia Repair", related pending U.S. Appl. No. 14/255,446, non-final office action dated Dec. 16, 2015.

Stephen Graham Bell, Giuseppe Amato, "Implant for Hernia Repair", related pending U.S. Appl. No. 14/255,446, applicants response to non-final office action filed Dec. 16, 2015.

Stephen Graham Bell, Wayne A. Noda, Giuseppe Amato, "Implant for Hernia Repair", related U.S. Appl. No. 14/516,005, Non-Final Office Action dated Feb. 25, 2016.

* cited by examiner

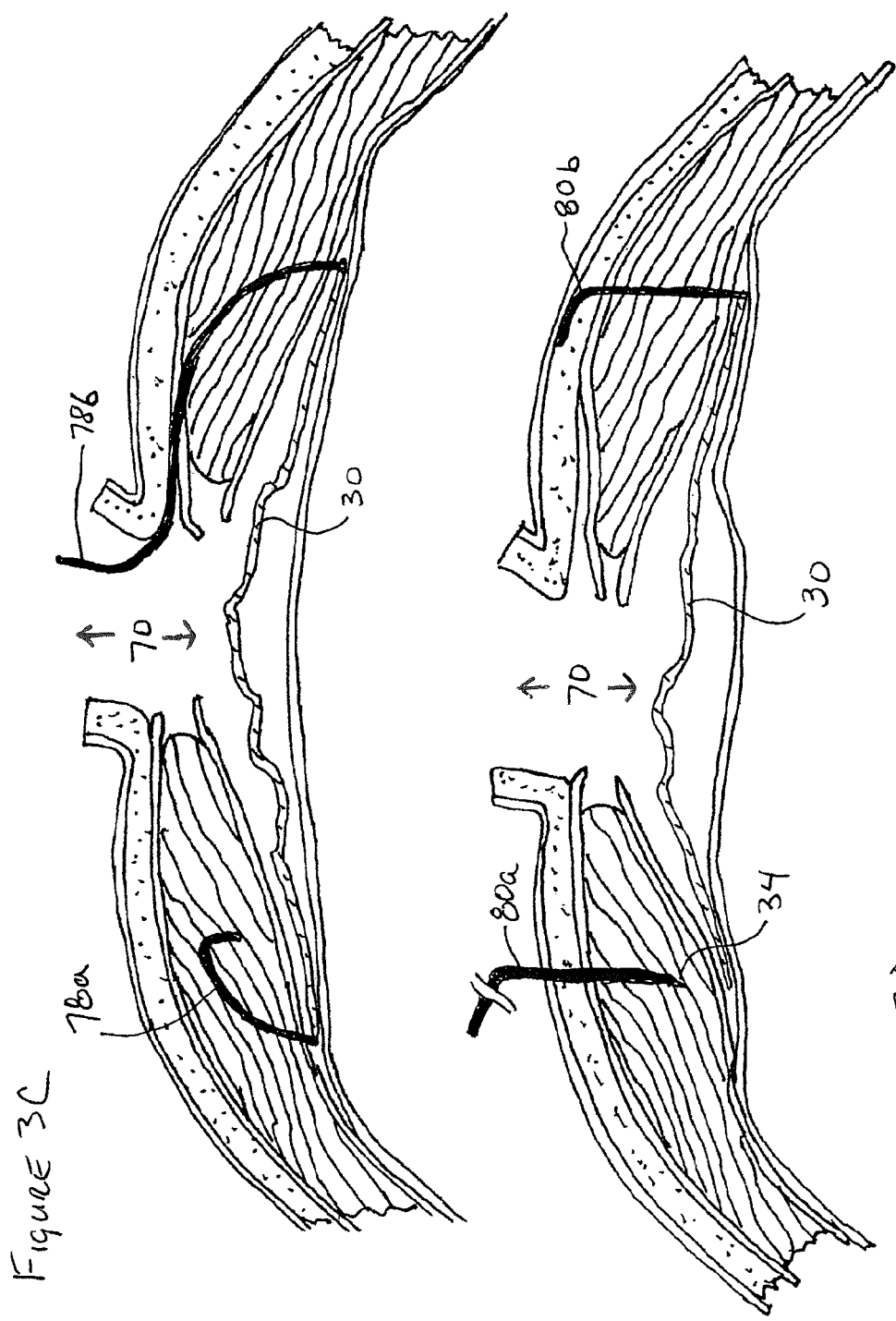

Figure 7D
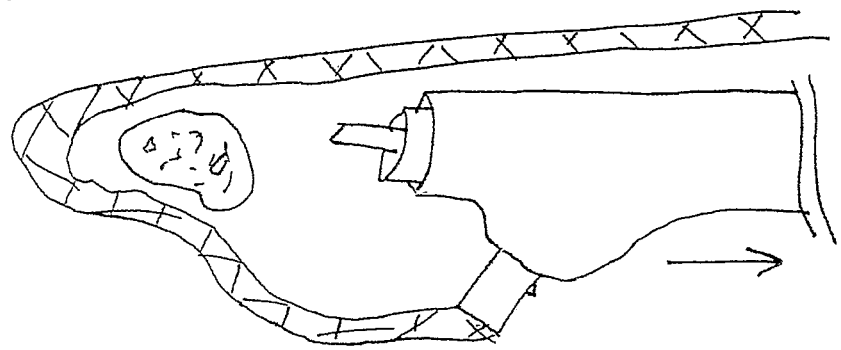
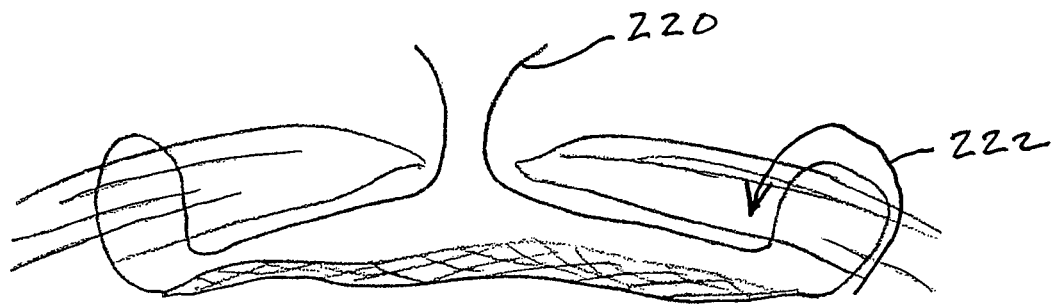
Figure 7E

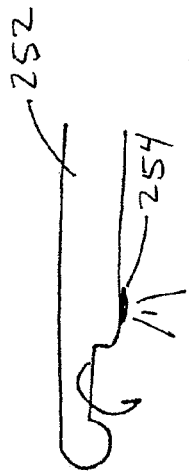
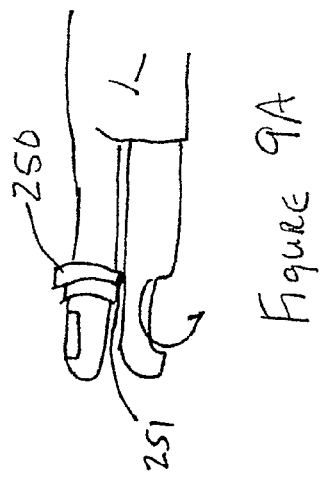
Figure 9A
Figure 9B
Figure 9C
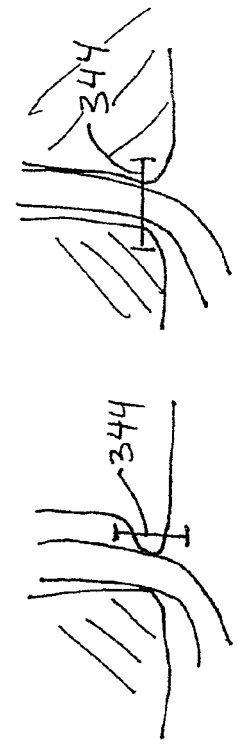
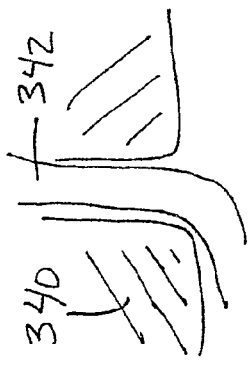
Figure 12

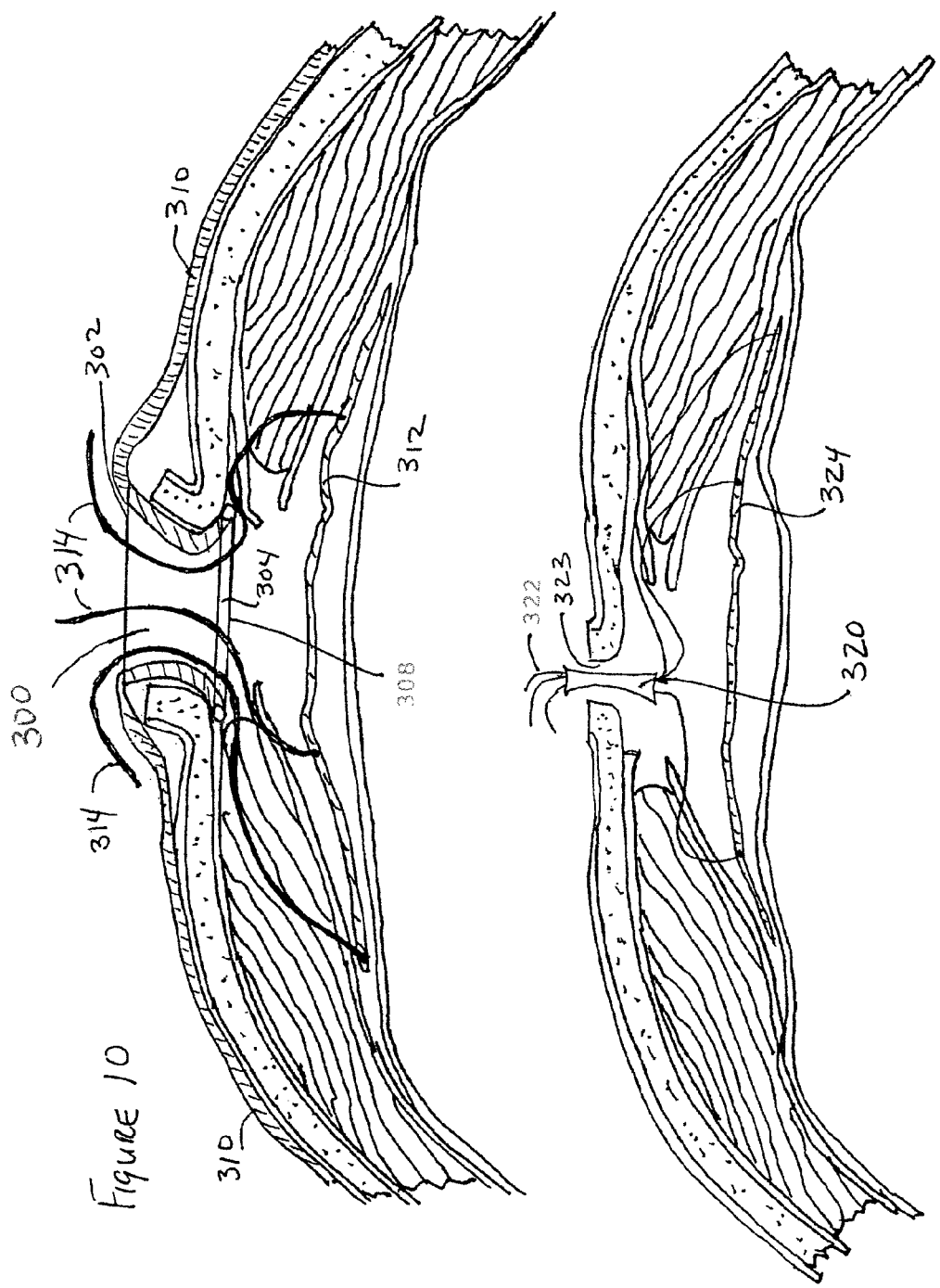

METHODS AND APPARATUS FOR TREATING VENTRAL WALL HERNIA

CLAIM OF PRIORITY

This application claims priority under 35 U.S.C. §119(e) to U.S. Provisional Application No. 61/013,619, filed Dec. 13, 2007, and U.S. Provisional Application No. 61/030,439, filed Feb. 21, 2008 the entire contents of which are hereby expressly incorporated by reference.

FIELD OF THE INVENTION

This invention relates to a surgical implant system for repairing abdominal hernias and is particularly useful for repairing ventral hernias. In particular, the present invention relates to an implant, an implant securement device, a delivery device and a method for implanting the implant.

BACKGROUND OF THE INVENTION

A hernia is a rupture of the abdominal wall which normally provides support for internal body organs. In conventional procedure for repairing a hernia, an incision is made over the site of the hernia, the internal viscera are pushed back into the abdominal cavity and the incision is closed by stitching or suturing one side firmly to the other. However this suturing can distort sensitive tissue, cause tension and subsequent pain, and often is not a permanent repair.

An alternative procedure which may utilize a laparoscopic approach involves placing a piece of knitted mesh material either over the hernial opening or inside the ventral wall opening, suturing or stapling the mesh material firmly in place to the ventral wall and closing the ventral wall opening. This procedure may be more permanent since tissue ingrowth into the mesh reinforces the weakened abdominal wall. However as the surgical site heals over time scar tissue may form which can lead to tissue movement, subsequent distortion of the implant and increased tension on the tissue and sutures adjacent the original repair. Other drawbacks to sutures, clips or staples is that prior to encapsulation they are susceptible to pulling out during coughing, extubation, etc. Once sutures or clamps are placed they also have no adjustability to even out the implant. This tension on the tissue can cause patient pain and discomfort. The hernia repair described herein happens after the procedure by inducing abdominal wall remodeling with an oversized mesh and thus it may reduce the problems associated with tension repairs Thus there is a need for an improved device and method for the treatment of ventral hernias and particularly one that reinforces the herniation, is secured to the ventral wall without tension and allows for tissue movement around the repair site.

SUMMARY OF THE INVENTION

The present invention provides for an improved device, system and method for the repair of ventral hernia and may solve the needs in the art stated above and may provide certain advantages over the prior art.

In one embodiment of the invention is a surgical implant having a tension free implant member that has at least one engagement member extending from the implant member. This engagement member is adapted to fixate the implant to at least a portion of the ventral wall such that when implanted the implant is in a substantially slackened condition relative to the ventral wall. The implant may be sized to be substantially larger than the hernia and may be a mesh that is made from a synthetic material, a biological material or a combination of materials.

In another embodiment of the invention the engagement member may comprise a strap, cord, suture or mesh. The engagement member may have a connector to connect the engagement member to the implant member. This connection is such that the engagement member may be fixated in an abdominal cavity independently from the implant member and then coupled to the implant member. The engagement member may have a piercing element such as a trocar, barb, hook, needle or guidewire, attached to one end that is designed to assist in securing the implant to the ventral wall.

In another embodiment, the engagement member may have a detachable zone formed from two ends joined together with a removable cord such that when the cord is removed or cut the two ends separate.

Another embodiment of the invention details a delivery device for securing an engagement member to the ventral wall and having a passer configured to penetrate at least a portion of the ventral wall. This passer may have a connector adapted to couple to the engagement member to pull the engagement member through the ventral wall. The passer may have a curved radius and a pivot point such that as the passer is advanced, the distal end penetrates tissue in a circular path. In use, when the passer is retracted, the engagement member is pulled through the circular path by the connector which may surround a tendon, bone, ligament, fascial tissue or a portion of muscle. Alternatively the passer may be made from a super elastic alloy having a pre-set radius with the passer confined by an outer tube such that as the passer is advanced from the tube, the distal end penetrates tissue in a substantially circular path which may surround a tendon, bone, ligament, fascial tissue or muscle portion.

In another embodiment of the invention the placement of the engagement member may be guided by the finger of the operator such that tactile feel of the operator can guide the apparatus to an particular anatomical position. And in another embodiment of the invention the placement of the engagement member may be guided by positioning the instrument using a light source coupled to a distal end of the instrument such that an operator can position the distal end by visualizing the light source through the skin.

Another embodiment of the invention is an apparatus for securing the engagement member to a portion of a ventral wall using a passer that may have an end adapted to penetrate the ventral wall in a substantially circular path when advanced. The apparatus may also have a strap tube that is connected to the engagement member and disposed about the passer. The apparatus may have a pusher also disposed about the passer with the pusher adapted to push the strap tube along the circular path of the passer.

In another embodiment the invention is a surgical kit containing an implant member, at least one engagement member and a delivery device for coupling the engagement member to at least a portion of a ventral wall. The kit may further include a passer with a distal end that is configured to penetrate a portion of the ventral wall. The kit may further include a connector attached to the passer end and adapted to couple to the engagement member so that the engagement member can be pulled through a portion of the ventral wall with the retraction of the passer. When the implant is secured to the ventral wall it may be in a substantially slackened condition relative to the ventral wall. The kit may also have a tunnel member with a drape attached to a wide opening of the funnel with one end of the funnel sized for placement into a surgical incision. The funnel member may have a retention ring formed adjacent to the narrow opening to retain the funnel in the incision.

Another embodiment of the invention is a method of treating a ventral wall hernia including the steps of creating an incision in the ventral wall, placing an implant having at least one engagement member into or along the interior ventral wall such that the implant is in a slackened condition relative to the ventral wall. The method may include pulling the engagement member through the ventral wall and through the skin. The method may also include detaching the engagement member from the implant prior to placement of the implant and pulling the engagement member first through the skin and ventral wall and attaching the engagement member to the implant. The method may also include pulling the engagement member through or around a tissue structure such as an abdominal muscle, ligament, tendon, or bone.

The method may also include positioning a delivery device having a passer adjacent a portion of a tissue structure and passing the passer through at least a portion of the tissue structure in a generally circular path. The method further including coupling a connector disposed at the distal end of the passer to an engagement member and pulling the engagement member through the tissue structure along the generally circular path by retracting the passer and connector.

Another embodiment of the invention may be a method including the steps of positioning an instrument having a passer in or alongside the ventral wall, passing the passer through a tissue structure of the ventral wall. The method including advancing a strap tube which is disposed about the passer and to which is connected to a distal portion an engagement member along the path of the passer by using a pusher.

Another embodiment of the invention is a method for treating a ventral wall hernia including the steps of creating an incision in the ventral wall, placing an implant having at least one set of opposing engagement members into or alongside the ventral wall and securing the implant to the ventral wall such that the implant is in a slackened condition relative to the ventral wall. The method may also include pulling the engagement members through the posterior ventral muscle fascia, around the ventral muscle and through the anterior ventral muscle fascia and then joining the opposing ends of the at least one set of engagement members together. An alternative embodiment of the method may include pulling the engagement members through the posterior ventral muscle fascia, around the ventral muscle and joining the opposing ends of the at least one set of engagement members together at a location disposed between the ventral muscle and the anterior ventral muscle fascia.

It is understood that both the foregoing general description and the following detailed description are exemplary and explanatory only and are not restrictive of the invention as claimed. The accompanying drawings illustrating an embodiment of the invention and together with the description serve to explain the principles of the invention.

BRIEF DESCRIPTION OF THE DRAWINGS

FIG. 3C is a cross-sectional view of an implant of FIG. 2 positioned in a herniated ventral wall and secured in a portion of the ventral wall;

FIG. 3D is a cross-sectional view of an implant of FIG. 2 positioned in a herniated ventral wall showing an alternative securement;

FIG. 7D is perspective view of the device of FIG. 7C with the passer and pusher withdrawn;

FIG. 7E is perspective view showing the device of FIG. 7D withdrawn leaving the implant and engagement member in the ventral wall;

FIG. 9A is a perspective view of a delivery device for securing an engagement member having a finger loop;

FIG. 9B is a perspective view of a delivery device for securing an engagement member having a light source;

FIG. 9C is a perspective view of a delivery device for securing an engagement member having an endoscope attached;

FIG. 10 is a perspective view of an embodiment of a surgical implant showing a funnel and drape;

FIG. 11 is a perspective view of an embodiment of a surgical implant showing retention tube.

FIG. 12 is a cross-sectional view of an implant positioned in a herniated ventral wall and secured with a set of engagement members over the anterior muscle fascia;

DETAILED DESCRIPTION OF THE PREFERRED EMBODIMENTS

Figure 1A:
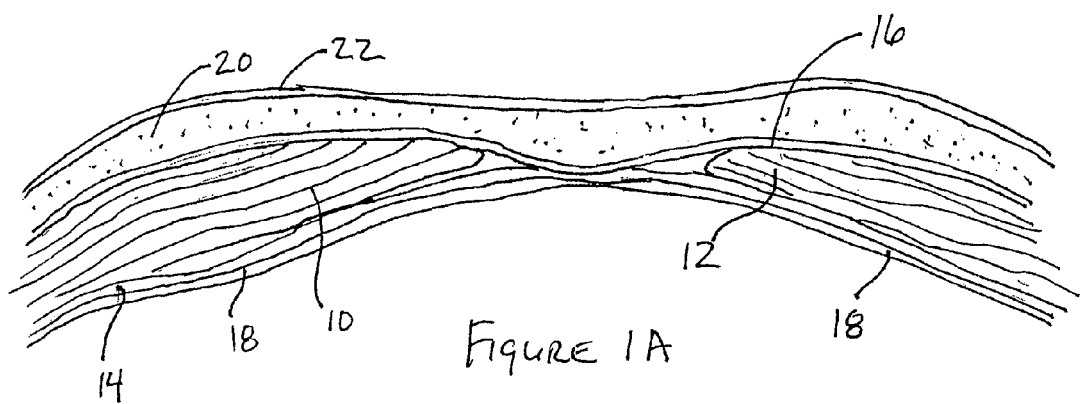
FIG. 1A is a cross-sectional view of a ventral portion of an anterior abdominal wall.

Although many different devices and several different methods of accessing and repairing abdominal hernias and in particular ventral wall hernias have been tried, including surgical and laparoscopic procedures, a better device and method is needed. Particularly a device that can be easily implanted and secured across the ventral wall and a device that allows for changes in the configuration and tone of the ventral wall as the hernia defect heals and remodels is necessary.

An implant and implantation method that permit small incisions, that can be implanted in a substantially slackened condition and have tension-free engagement members to accommodate changes in the healing/remodeling of the ventral wall may lead to better outcomes.

Although the repair of ventral hernias is particularly referenced, it is anticipated that the apparatus and methods described herein may be used for other surgical or laparoscopic procedures whereby a tissue structure of the human body requires strengthening or supporting. The delivery devices described are applicable to hernia repair but may be used wherever a strap, cord, engagement member or suture needs to be passed through a tissue of the body. Although shown in the ventral portion of the abdominal wall and although so described for treatment of ventral hernias, the apparatus and methods shown may be used for inguinal hernias, pelvic support, and other areas of the body.

Many other hernia repair devices are positioned in the hernia and then fixated in place using rigid clips, sutures or staples. These fasteners securely attach the implant to the abdominal wall and prevent migration of an implant over time. However these securement practices do not allow for the expansion or contraction of the surrounding tissue as part of the healing process. It has been found that the tissues of the abdominal wall change over time as the tissues heal and as abdominal wall tissue invades the implant, particularly a mesh implant. While this cell in-growth may provide a cell impregnated structure that is strong and biocompatible, it is also inflexible and incapable of accommodating tissue movement or expansion. In particular scar tissue typically forms and as it develops the tissues surrounding an implant may be pulled and stretched due to shrinkage of the encapsulated mesh. If an implant is directly and rigidly stapled or clamped to the ventral wall, these rigid attachments can tear out over time resulting in the potential for a reoccurrence of the hernia and discomfort for the patient.

Therefore one preferred embodiment of the invention is configured to be implanted into an abdominal cavity in such a way that a tension free condition results. This tension free condition is one in which the implant is placed into position with sufficient slack so that as surrounding tissue expands or moves, this implant slack can be used to avoid pulling and possible tearing of surrounding tissue that may result from an implant that is too tight or does not have any residual slack. Additionally, the implant may be configured with engagement members or straps that are used to at least temporarily secure the implant to the surrounding tissue and retain mesh orientation. These engagement members may be secured to tissue such that they are tension free. Tension free means that these straps are not rigidly secured to tissue with a staple or clip but rather are held in place by friction generated between the engagement member and surrounding tissue. In this condition these members secure and stabilize the implant but also permit some movement of the engagement member relative to surrounding tissues over time. The tension free engagement members and the oversized implant with substantial slack allow for longer term natural abdominal wall remodeling which is may be particularly important to reduce and fix the hernia. It is believed that this type of tension free implant may promote better healing, reduce premature tear-out or dislodgement or dislocation and provide increased comfort and acceptance by the patient.

Figure 1B:
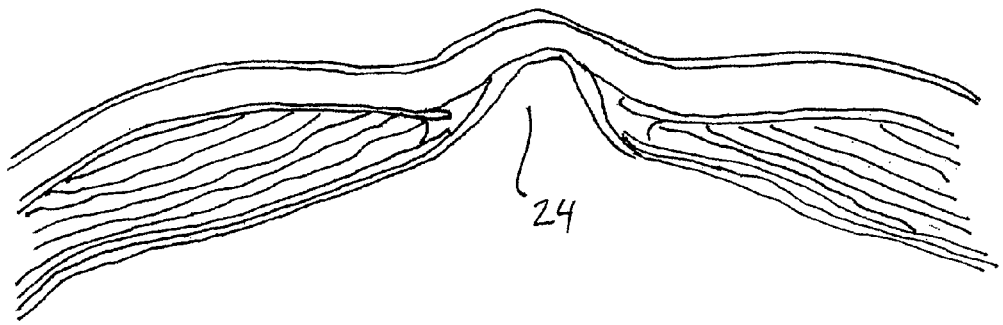
FIG. 1B is a cross-sectional view of FIG. 1A showing a herniation in the ventral wall.

Referring to FIG. 1, there is shown a cross-sectional view of a normal, anterior abdominal wall of the ventral region of the body. The abdominal wall includes left and right rectus muscles 10 and 12 enclosed and held in place by posterior layers of fascia 14 and anterior layers of fascia 16. These layers of fascia, which are thin, strong fibrous tissue, merge together in the region intermediate the rectus muscles 10 and 12. A thin layer 18, called the peritoneum, covers the posterior side of the posterior fascia 12. The peritoneum 18 is a soft, pliable layer of tissue material and provides an enclosure for the intestines and other internal viscera. A layer of skin composed of the sub dermis 20 and dermis 22 covers the exterior of the anterior fascia 16. FIG. 1B illustrates a condition where a hernia has formed in the wall of the abdomen. The hernial opening is shown at 24. In this example, the hernia is formed by the rupture of the fascia layers 14 and 16 in the region intermediate the rectus muscles 10 and 12. This rupture permits the internal viscera to push the peritoneum 18 in an outward direction, creating a bulge 24 in the skin layers 20 and 22. If not treated, the condition will only worsen with time, with the peritoneal bulge becoming larger.

Figure 2:
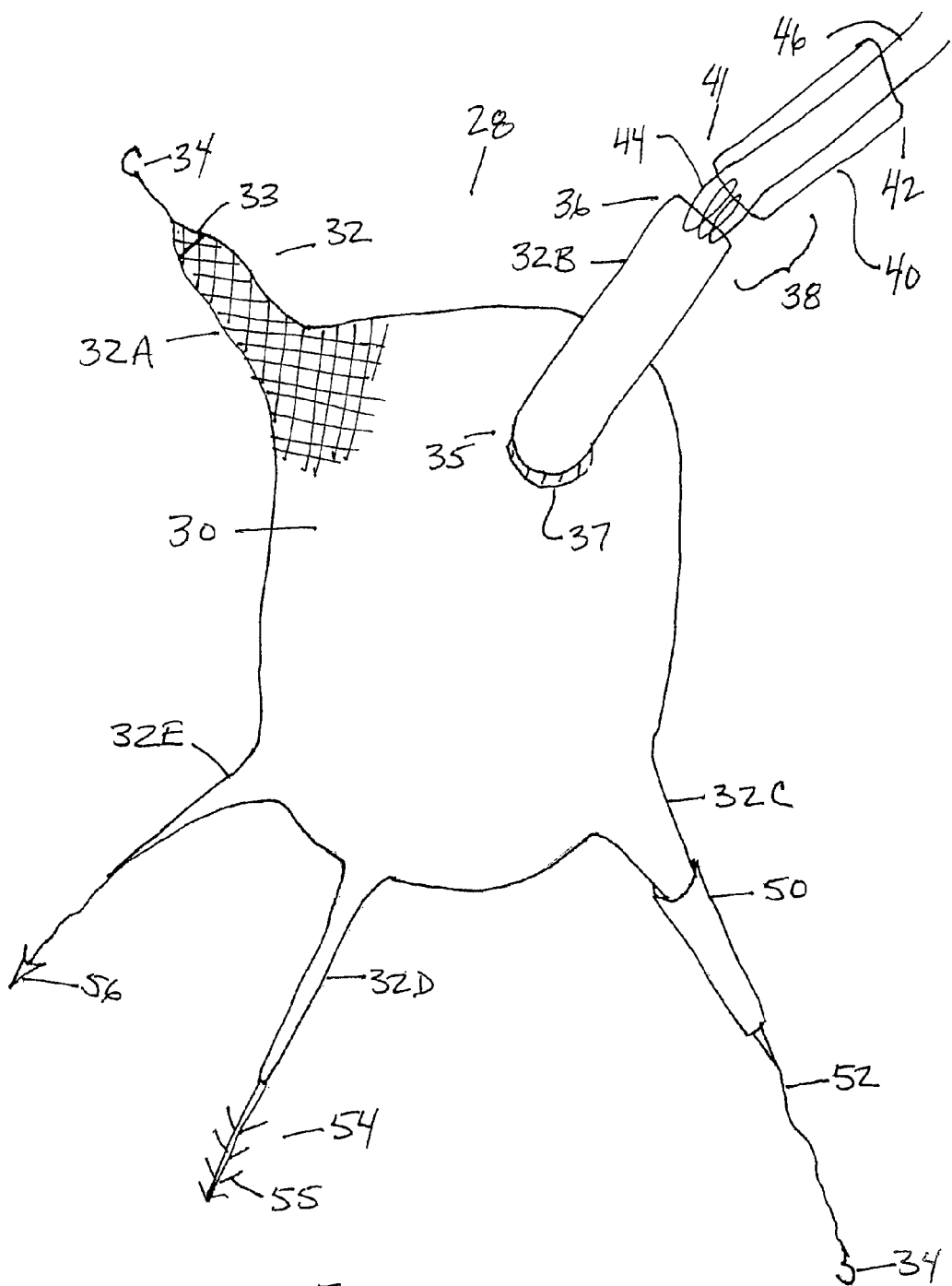
FIG. 2 is a perspective view of an embodiment of a surgical implant.

Referring now to FIG. 2, there is shown a surgical implant or a hernia repair device 28 comprised of an implant member 30, also referred to as an implant, and having at least one flexible engagement member 32A-E extending from the side of the implant. The implant 30 may be constructed of a solid or a permeable material. The implant 30 may have various shapes. An example of a permeable material is a mesh that may be receptive to tissue ingrowth. Suitable materials for making the mesh may be: polypropylene mesh such as that distributed by C. R. Bard, Inc. of Murray Hill, N.J. under the trade name "Marlex"; a polyethylene mesh material of the type distributed by E. I. Du Pont de Nemours and Company of Wilmington, Del. under the trade name "Alathon"; and a Dacron mesh material or a Nylon mesh material of the type distributed by E. I. Du Pont de Nemours and Company of Wilmington, Del. Additionally the mesh may be constructed from a metallic mesh or a polymer mesh having interwoven metallic filaments. These filaments may provide additional strength to the mesh or make the mesh radiopaque for later visualization. The mesh may be a single layer or have a multilayer construction. The mesh may have one or more layers constructed from a bioabsorbable material such that the mesh may be reabsorbed by the body over time. The mesh may have one or more layers constructed from a layer having anti-adhesion properties such that ingrowth or attachment of tissue to the mesh is inhibited. One or more layers may also be coated with an anti-adhesional coating that is applied to a surface to inhibit tissue attachment. These anti adhesional characteristics may be particularly useful for those implant surfaces that are exposed to the internal viscera of the abdominal cavity. In this situation it may be helpful to inhibit potential attachment of various organs to the implant. This may be particularly possible if the innermost surface of the ventral wall, the peritoneum 18, is compromised. One example of an adhesion resistant material is, for example, a thread of polytetrafluoroethylene polymer material of the type sold under the trade name "Gore-Tex" by W. L. Gore & Associates, Inc.

The implant 30 may be made initially oversized compared to the size of the hernia. The implant may be sized substantially larger than the area of the hernia and may comprise an area equivalent to the area encompassed by a patient's diaphragm and pubis in one direction and the lateral sides of a patient's abdomen in the other direction. A large implant 30 may improve adhesion to the abdominal wall. An implant sized substantially larger than the hernia may preferably be 1.5 times larger than the area of the hernia, or more preferably two times larger than the area of the hernia, or most preferably multiple times the size of the hernia area. In another embodiment the implant is oversized compared to the area of the hernia, but the implant 30 is trimmable. That is the implant may be trimmed in situ to fit the size of the hernia. In this way one implant size may be provided to the user and then the implant custom trimmed to fit the surgical conditions.

The engagement member 32A-E may be used to secure the implant 30 to the ventral wall and if more than one engagement member 32 is used then they are preferably symmetrically arranged around the perimeter of the implant 30. Although five engagement members 32A, 32B, 32C, 32D, and 32E are shown in FIG. 2, this is for descriptive purposes only. The apparatus 28 may use one, two, four or more engagement members. The placement of the member may be at an apex of the implant 30 or evenly spaced around the perimeter. The member may be integrally formed as an extension of the implant 30 or may be a separate piece that is formed from the same material as the implant 30. The member and the implant 30 may also be constructed from different materials. The member may be identified with unique identifying characteristics so that one member may be discerned from another. In this way a member corresponding to a particular location on the implant may be identified. By way of example that is not meant to be limiting, each member may have a different color coding so that when the implant is inside the abdominal space, the orientation of the implant may be discerned and correct positioning of the members to avoid entanglement can be realized.

The engagement member may have different configurations and the device 28 may utilize one configuration only for a particular implant or multiple configurations may be utilized on a single implant. However the engagement member is generally flexible and not rigid. While other prior art devices utilize stiff and rigid engagement type members and especially rigid placement needles or trocars, the present invention is flexible. The members are adapted to pass through ventral wall tissue structures such as the posterior and anterior fascia layers 14 and 16, rectus muscles 10 and 12, sub dermis 20 and dermis 22. Member 32A is shown as a woven mesh that is integrally formed as an extension of the implant mesh 30. In this configuration the member 32A is a mesh strap that may extend 2-20 inches from the perimeter of the implant 30. As can be shown the member 32A has a tapered end 33 that reduces the width of the strap to taper to a point of attachment to a piercing element 34. The piercing element 34 is formed as a part of the strap or may be attached at end 33. The piercing member has a sharpened end adapted to pierce tissue structures so that the member 32A may be pulled through the tissue structures similar to a needle and thread using a delivery device to be illustrated later. Alternatively the member 32A may be pushed through the tissue structures. The piercing member may be a trocar, barb, hook, needle or a passer element such as a guidewire.

Engagement member 32B having an inner end 35 and an outer end 36, is shown coupled to the implant 30 at inner end 35. Inner end 35 is located interiorly from the perimeter of the implant 30. This attachment location may facilitate trimming the implant area at the interventional site because the attachment point is set apart from the edge that might be trimmed. The attachment location could be located anywhere on the implant and is not limited to a particular location. Secondly, member 32B is not integral to the implant 30 but is a separate member. Member 32B is attached to the implant with a connector 37 at the end 35 of the member 32B. This member may be deployed as part of the implant or may be decoupled from the implant and re-coupled later. This configuration of implant allows separate placement of the member and implant. In some situations it may be preferable to position the member 32B prior to insertion of the implant. In other situations it may be preferable to position the member after the implant is positioned. The connector 37 may be any type of mechanical connector, magnetic connector, adhesive or other connector. Some examples of mechanical connectors are hooks, snaps, threaded sections, bayonet fastener, hook and loop type fastener, snares, buttons, suture, or clamps although any type of connector may be suitable and this list is not meant to be limiting.

Engagement member 32B also has a detachment zone 38 that is the coupling zone for the member 32B and the extension element 40. Extension element 40 has inner and an outer ends 41 and 42. The inner end 41 of the extension element 40 is coupled to the outer end 36 with the use of cord 44. The cord 44 may be a thread, suture or other similar material configured so that the two described ends 36 and 41 can be coupled by loosely tying them together. An end of the cord 46 may extend outside the body. Together the engagement member 32B and the extension 40 provide a long enough length of strap so that the combination can be used to tension the implant by pulling the extension element 40 from outside the body. However, once the implant is tensioned properly any excess engagement member is unnecessary and is often removed so that the end of the engagement member can be positioned inside the incision. Therefore the excess may be cut away but the optimal cutting point may be deep inside the ventral wall and difficult to reach especially with a small incision. Therefore the detachment zone 38 is intended to provide a remote method of detaching unneeded length of the engagement member that is inside the incision. The cord 44 may be severed at the detachable zone 38 with a blade or may be released by pulling on the cord end 46 from outside the body. In another embodiment of the invention the engagement member 32B terminates at outer end 36 and extension element 40 is not present. However cord 44 may still be threaded through the outer end 36 only. Tension may be applied to the engagement member by pulling on the cord 44. After proper positioning and tensioning of the implant 30, the cord may be removed from the engagement member 32B by pulling on the cord end 46 so that the outer end 36 remains inside the ventral wall cavity.

In another embodiment of the engagement member 32C, the width of the member is reduced to facilitate pulling the engagement member through various tissue structures. The reduced lateral profile may reduce friction and the resultant force required to pull or push the engagement member. The engagement member 32C profile may be reduced by spinning, forming or winding the member 32C material into a smaller diameter and thereby forming a cord or leader. The engagement member 32C profile may be reduced by the use of a sleeve 50 disposed around the member. Such a sleeve 50 may be made of polyethylene, polypropylene, nylon, silicone or other suitable polymer that may be useful to reduce the friction as the engagement member passes through tissue structures. The sleeve 50 may be made from a shrink tubing. Engagement member 32C may have all or a part of its length comprised of a leader 52. This leader may be made of suture, cord, string, wire or other suitable flexible material. This leader 52 may be coupled directly to the implant 30 or may comprise a portion of the engagement member 32C. The leader may terminate at its outer end with a piercing member 34 as shown previously.

The outer end of the engagement member may also terminate with an anchor 54 or 56 attached to engagement members 32D and 32E. Engagement members 32D and 32E may be positioned in a tissue structure either by pushing or pulling the members as will be shown. These members' outer ends enter tissue structures and then anchor into the tissue to secure the engagement member to the tissue. Various anchor designs are anticipated and the anchors 54 and 56 are not meant to be limiting. Anchor 54 is shown having lateral barbs 55 that may have a fixed configuration or these barbs may be deployable after positioning. The anchor 56 is a barbed hook which may pass easily into tissue and then inhibit reverse movement to prevent pullout of the anchor and engagement member.

Figure 3A:
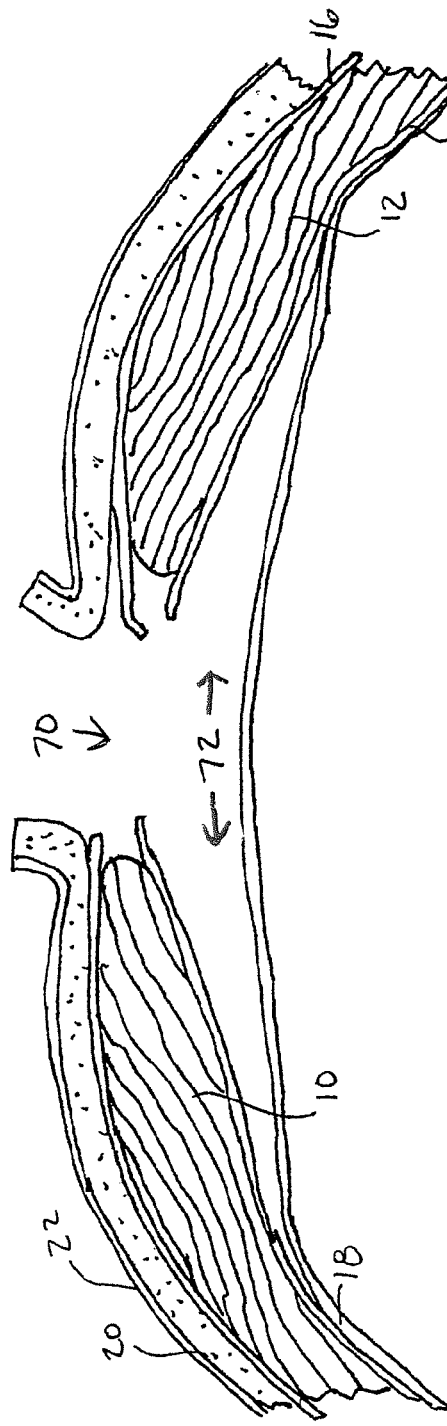
FIG. 3A is a cross-sectional view of a herniated ventral wall prepared for positioning an implant.

Referring now to FIG. 3A, shown is a cross-sectional view of a herniated ventral wall prepared for positioning of an implant. An incision 70 has been made along the midline preferably along a line running from the diaphragm to the pubis and laterally; toward the sides of the abdomen. The incision size may be smaller than other surgeries since the securement of the implant utilizes engagement straps to secure the implant to the ventral wall and the kit may include a delivery device that is capable of securing the engagement member from inside a small incision. This eliminates the current method of suturing which often requires more access.

The incision size may also be smaller than other surgeries since the securement of the implant and does not utilize bulky staplers to secure the implant 30 to the ventral wall. Direct placement of larger implants or the use of staplers may require more operating space and thus a larger incision size than contemplated with this apparatus. The tissue has been dissected down to the level of the peritoneum 18 and a pocket or cavity 72 has been formed between the posterior fascia 14 and the peritoneum 18 to receive the implant.

Preferably the implant is placed into a pocket 72 as described however other pocket locations such as between the fascia and the rectus muscle, between the rectus muscle and the anterior fascia or between portions of the skin are also possible. If the peritoneum 18 is not continuous, the peritoneum may be approximated before implant placement. If such approximation is not possible, then the implant may be implanted without a pocket and may be placed along the posterior side of the peritoneum if necessary. Various implant configurations described previously including those having anti-adhesion coatings or layers may be used if the peritoneum is not continuous. These coatings or layers are intended to inhibit attachment of the implant to internal viscera.

Figure 3B:
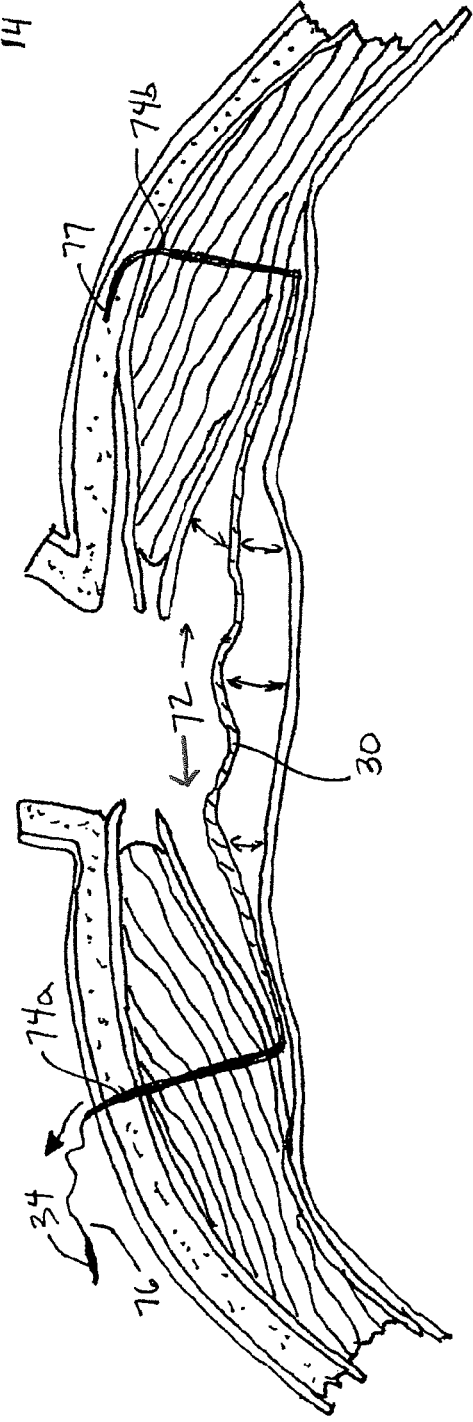
FIG. 3B is a cross-sectional view of an implant of FIG. 2 positioned in a herniated ventral wall and secured generally through the skin.

As shown in FIG. 3B, an implant 30 has been sized and positioned in pocket 72. The implant may be made having one size and then may be cut and trimmed in situ so that the implant is properly sized according to the size of the pocket formed. However several different sized implants may be made to accommodate various pocket and hernia sizes expected. The implant 30 is positioned between the peritoneum 18 and the posterior fascia 14 and is secured in position by engagement members 74a and 74b.

As shown the implant is implanted in a substantially slackened condition as shown by the large gaps indicated by open double arrows shown between implant 30 and the peritoneum 18 and the posterior fascia 14. An implant that is positioned with a slackened condition means that the implant is not tight against tissue structures but is loosely positioned and gaps are present between the implant and these tissue structures. This slack may be useful as the surrounding tissue moves or expands as a result of the healing process. The slack means no tension is made when the mesh and tissue ingrowth shrink this eliminates pain associated with current repairs that great massive tension on the sutures or staples.

This slack may be reduced as the ingrowth tissue shrinks and contracts. The gaps shown may be equivalent to between one implant thickness and multiple implant thicknesses. The amount of slack in the implant may be directly observed through the incision 70 and may be adjusted by extending or retracting the engagement members 74a and 74b from the tissue structures. As shown, the engagement members are secured by friction generated between the member and the tissue structure. The members may be secured to the tissue by using a curved pathway through the tissue to increase the friction described. Alternately the members may utilize barbs or serrations to increase the securement of the members to surrounding tissue.

As shown by the single arrow, the engagement member 74a is deployed through the entire ventral wall by pushing the flexible engagement member 74a having a piercing member 34 at its outer end 76. This piercing element 34 pierces tissue and facilitates insertion through the various tissue layers previously described. This type of placement may be referred to as an in/out technique in that the member passes from inside the body toward the outside of the body. The engagement member 74a extends past the dermis and the tension on the implant 30 may be adjusted by pulling on the outer end 76 of the member. Thus once the member 74a is pushed through the skin by a physician, the outer end 76 may be pulled as the implant slack is visualized through the incision 70 until the desired slackened condition is reached. The engagement members are thus in a "tension-free" condition in that they are not rigidly anchored to tissue structures with sutures, clips or staples as other devices. However the pathway through the tissue structures provides enough friction on the engagement members to secure them and the attached implant in place. Engagement member 74*a* is shown extending through the entire ventral wall and exiting through the skin but the member 74*a* may extend only partially through the ventral wall.

Engagement member 74*b* is shown with the outer end and piercing element removed and the new end 77 positioned subcutaneously. Once the engagement member 74*a* is inserted through the ventral wall and the implant 30 tensioned appropriately, the outer end 76 and piercing element 34 may be removed and the end 77 tucked under the skin using common surgical practice. Although two engagement members are shown, any number of members may be used to secure an implant. Preferably two, or four or six members may be used to secure the implant to the ventral wall. Turning now to FIG. 3C, alternative configurations of apparatus and method may be utilized to secure the engagement member to surrounding tissue structures. Engagement member 78*a* is shown deployed partially through the ventral wall and terminating in the rectus muscle. A complete puncture of the skin may not be required to secure the implant. Various portions of the ventral wall may be used to secure the member 78*a*. Also other tissue structures may be used to secure the member. For example tendon, bone, ligament, fascial tissue or various muscle portions may be used to secure the member. The member may encircle these structures to increase the surface area contact, increase the friction, and provide a stable anchor point and thus the holding strength of the member on the implant.

In another embodiment, an engagement member 78*b* is deployed through the posterior fascia, rectus muscle, anterior fascia and then through the incision opening 70. In this configuration, the outer end of the engagement member 78*b* is easily accessible so that the outer end may be pulled to tension the implant. Excess member material may be removed and the end tucked inside the incision 70.

Alternately an engagement member may be inserted from outside the body through the skin to the implant. This type of placement may be referred to as an out/in technique in that the member passes from outside the body toward the inside of the body. As shown in FIG. 3D, an engagement member 80*a* is partially deployed through the skin in the direction of the arrow. The member 80*a* has a piercing element 34 at the end to facilitate insertion of the member 80*a* through the ventral wall. The member 80*a* may have a connector located at the same end to connect with the implant 30 once the member 80*a* is fully positioned. Alternatively the piercing element 34 may also function as a securement device. An example of this may be a barbed hook. Once attached to the implant, the member may be pulled in a direction opposite the arrow to tension the implant. Similarly to engagement member 74*b*, the outer end of the member may be removed and the end tucked under the skin as engagement member 80*b*.

Figure 4A:
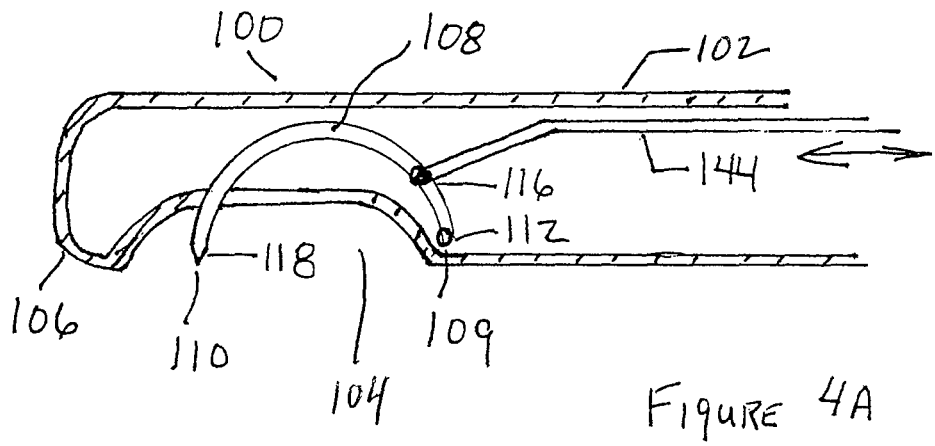
FIG. 4A is a perspective view drawing of an embodiment of the present invention showing an apparatus for securing an engagement member to a ventral wall.
Figure 4B:
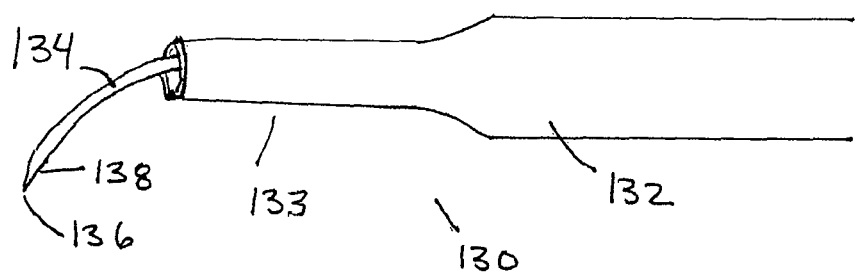
FIG. 4B is a perspective view drawing of an embodiment of the present invention showing an alternate apparatus for securing an engagement member to a ventral wall.
Figure 4C:
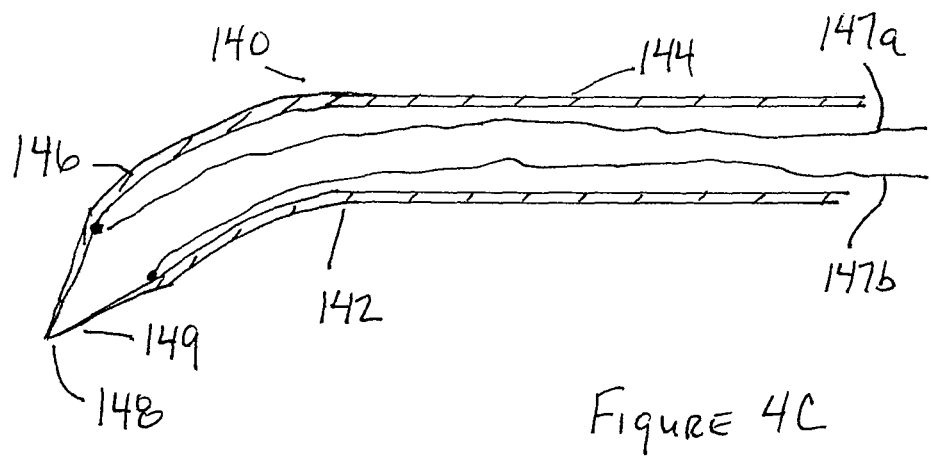
FIG. 4C is a perspective view drawing of an embodiment of the present invention showing an another alternate apparatus for securing an engagement member to a ventral wall.

Referring to FIGS. 4A-C, three embodiments of a delivery device to position an engagement member are illustrated. Such a delivery device and method may be used to position an engagement member in a tissue structure through a confined space with little visibility such as found in the incision and small pocket described previously. An intended benefit of the described delivery device and method is to position an engagement member as previously described through a smaller incision as with other devices.

The delivery device 100 includes a housing 102 having a cavity 104 disposed at its distal end 106. A curvilinear passer 108 having an inner end 109 and an outer end 110 is disposed inside the housing 102. The outer end 110 is sharpened to facilitate passage through tissue structures. The inner end 109 is coupled to the housing 102 at a rotating pivot 112 so that the passer can rotate about this pivot in a generally circular pathway. The term circular path is meant to include generally curved paths and other path shapes that are not considered straight or substantially straight, and paths that generally extend from the cavity 104 to the housing 102 as will be shown. The passer 108 is rotatably linked to an actuator 114 at linkage 116 and the actuator is slidably disposed inside the housing. The outer end 110 of the passer may also have a connector 118 that is adapted to couple to an engagement member.

Figure 5A:
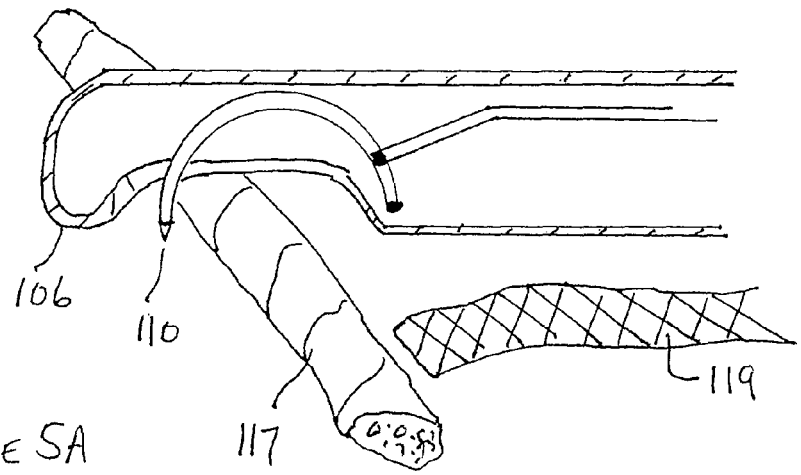
FIG. 5A is a perspective view of a delivery device for securing an engagement member to a ventral wall.
Figure 5B:
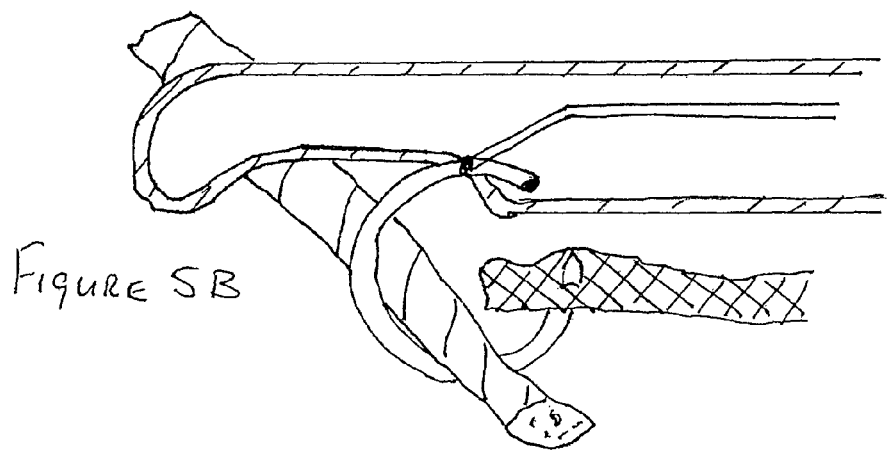
FIG. 5B is a perspective view of the delivery device of FIG. 5A showing a passer having a generally circular path around a tissue structure.
Figure 5C:
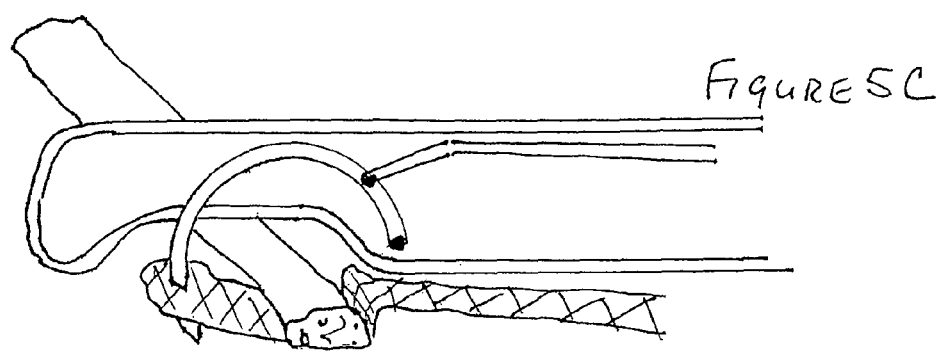
FIG. 5C is a perspective view of the delivery device of FIG. 5B showing the engagement member being pulled by the passer.

As shown in FIGS. 5A-C, the delivery device 100 of FIG. 4A is positioned at the delivery site with the cavity facing the direction of activation. As the actuator 114 is moved toward the distal end 106, the passer 108 is driven through the linkage 116 and pivots around the pivot 112. The passer then moves in a generally circular pathway that conforms to the shape of the passer into or around tissue structures 117 located inside or adjacent the cavity. The mechanism may be useful to drive the passer 108 around tissue structures 117 such as tendon, bone, ligament, fascial tissue or portions of muscle. As the passer traverses in a generally circular pathway, it may couple with an end of an engagement member 119 by passing the connector 118 through the engagement member that has been positioned nearby. The connector shown is a barbed hook that penetrates the mesh of the engagement member 119.

Once the engagement member 119 is coupled to the connector 118, the actuator may be retracted away from the distal end 106 which also retracts the passer 108. This movement pulls the engagement member 119 along the generally circular pathway of the passer, and back into the housing. The delivery device 100 may be withdrawn in the direction of the arrow, pulling the engagement member through or around the tissue structures. In the case of ventral hernia repair, the delivery device 100 maybe used to position the engagement members in or around various tissue structures such as the fascia layers, rectus muscles, and dermis and sub dermis layers.

An alternate delivery device 130 is shown in FIG. 4B including a housing 132 having a tapered end 133 with a passer 134 slidably disposed inside. The passer 134 may have a sharpened end 136 and a connector 138 to couple with an engagement device. The passer is made from a curved superelastic alloy such as Nitinol. The passer 134 is restrained inside the housing and when advanced outside the housing, the passer assumes a curved shape. The passer is driven through tissue structures as it is further advanced from the housing traversing a generally circular pathway. The connector 138 located at the sharpened end 136 is adapted to couple with an engagement member such that as the passer is retracted inside the housing 132, the engagement member (not shown) is pulled through the generally circular pathway of the passer. The mechanism may be useful to drive the passer around tissue structures such as tendon, bone, ligament, fascial tissue or portions of muscle. The delivery device 130 may be withdrawn pulling the engagement member through the tissue structures. In the case of ventral hernia repair, the delivery device 130 maybe used to position the engagement members in various tissue structures such as the fascia layers, rectus muscles, and dermis and sub dermis layers.

An alternate delivery device 140 is shown in FIG. 4C having a passer 142 comprising an elongate hollow housing 144 coupled with a steerable end portion 146. Disposed inside the hollow housing are at least two controlling wires 147a-b that extend to the proximal end. These controlling wires are attached to the steerable end portion 146 such that by relaxing one wire and pulling another the steerable end portion may be actuated to steer the steerable end portion 146 in a particular direction. As can be seen, if the wires are positioned next to a tissue structure and actuated to form a curved configuration, as the passer 142 is advanced the passer will traverse through a generally circular pathway. The passer may have a sharpened end 148 and a connector 149 located at the end. The connector 149 is adapted to couple with an engagement member such that as the passer 142 is retracted and the steerable end portion is straightened, the engagement member (not shown) is pulled through the generally circular pathway. The delivery device 140 may be withdrawn pulling the engagement member through the tissue structures. In the case of ventral hernia repair, the delivery device 140 maybe used to position the engagement members in various tissue structures such as the fascia layers, rectus muscles, and dermis and sub dermis layers.

Figure 6A:
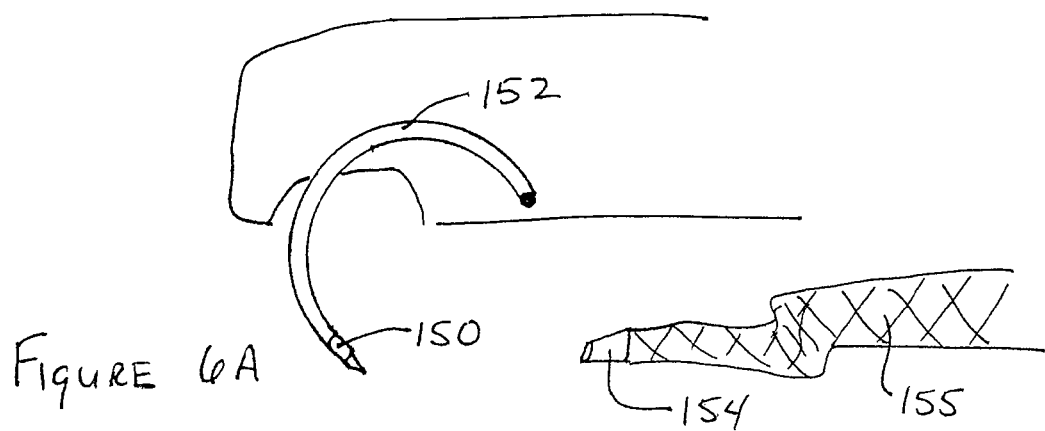
FIG. 6A is a perspective view of an embodiment of a delivery device for securing an engagement member showing a passer with a connector and an engagement member with a receiver.
Figure 6B:
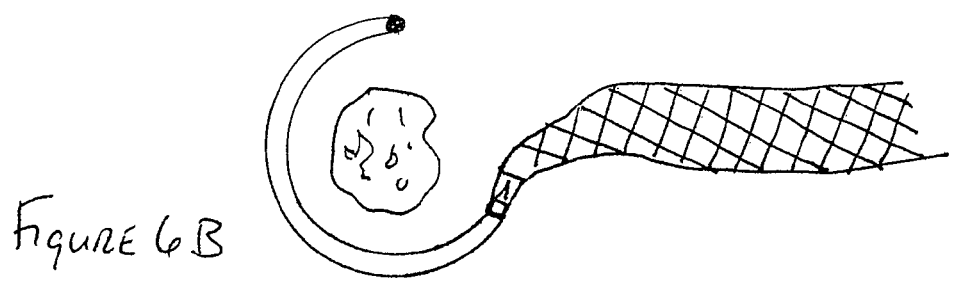
FIG. 6B is a perspective view of a delivery device of FIG. 6A showing a passer and engagement member connected using the connector and receiver.
Figure 6C:
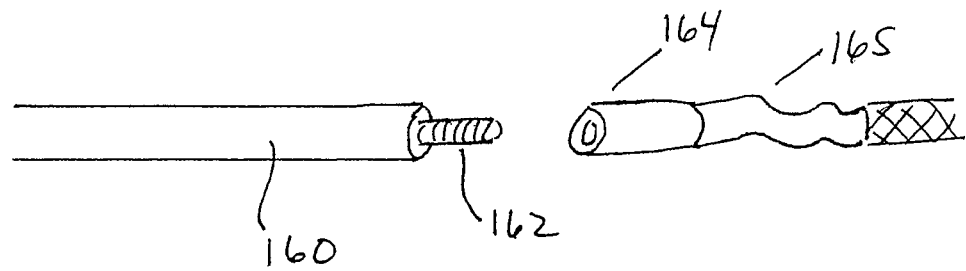
FIG. 6C is a perspective view of a passer with a threaded connector and an engagement member with a threaded tube.
Figure 7A:
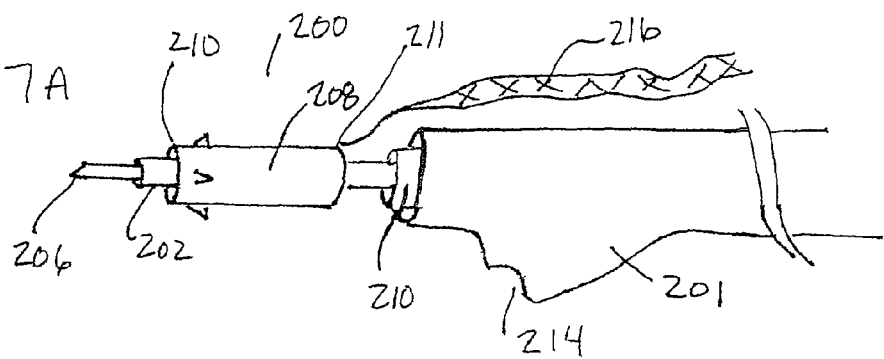
FIG. 7A is a perspective view of an embodiment of a delivery device for securing an engagement member to a tissue structure.
Figure 7B:
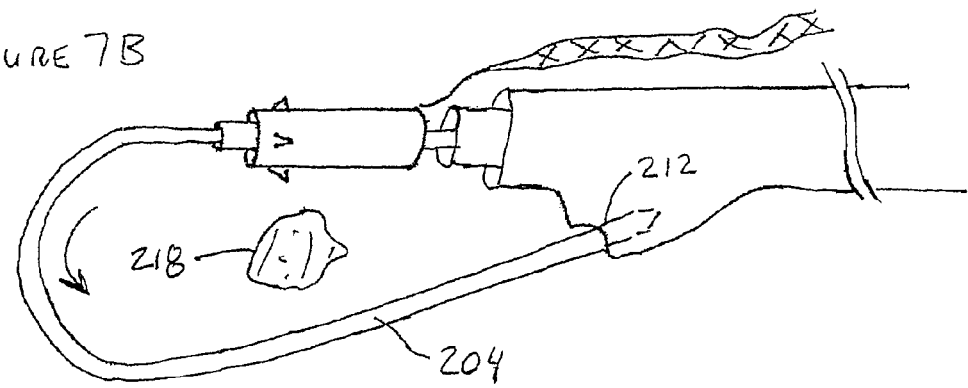
FIG. 7B is a perspective view of the device of FIG. 7A showing a deployed passer.
Figure 7C:
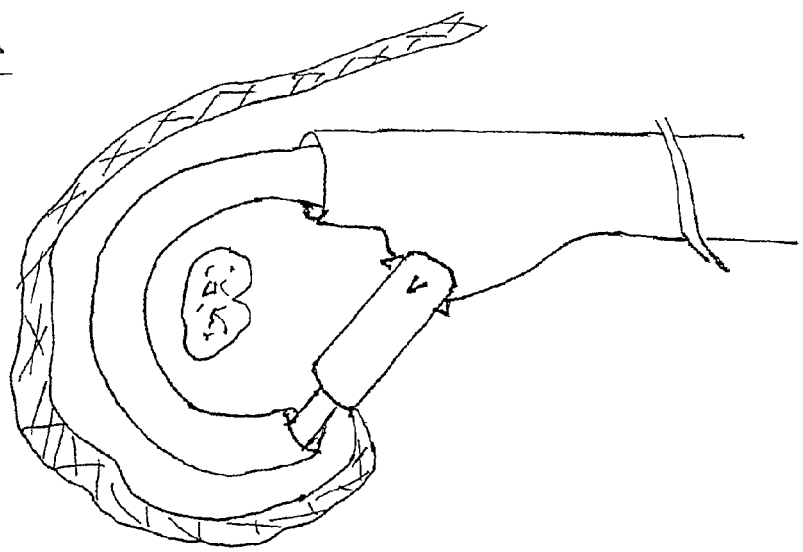
FIG. 7C is perspective view of the device of FIG. 7B with a pusher and strap tube deployed.
Figure 8A:
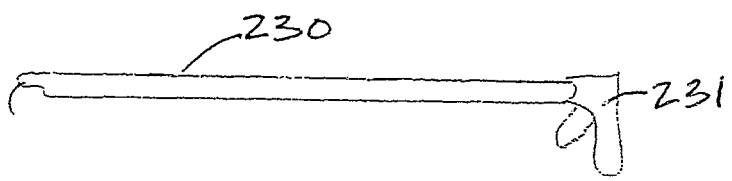
FIG. 8A is a drawing of an alternative shape of a delivery device for securing an engagement member showing a substantially straight shape.
Figure 8B:
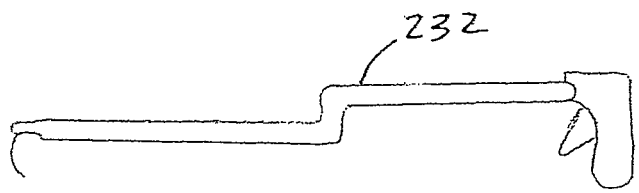
FIG. 8B is a drawing of an alternative delivery device for securing an engagement member showing an offset straight shape.
Figure 8C:
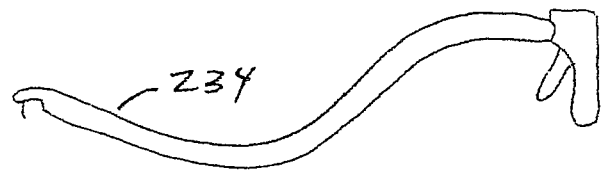
FIG. 8C is a drawing of an alternative delivery device for securing an engagement member showing a curved shape.
Figure 8D:
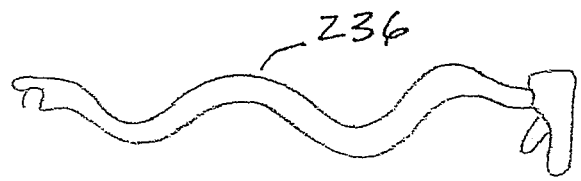
FIG. 8D is a drawing of a flexible delivery device for securing an engagement member.

Alternate connectors are illustrated in FIGS. 6A-C that may be useful to connect a previously described passer with an engagement member. A connector 150 is shown attached to a passer 152 similar to those discussed. The connector 150 may be a magnet tip that is configured to mate with a magnetic receiver 154 attached to an engagement member 155. As the magnetic tip passes through tissue structures and approaches the magnetic receiver 154, a magnetic coupling occurs and the engagement member 155 is detachably joined to the connector and passer. The magnetic coupling should be strong enough to maintain the coupling as the passer is withdrawn pulling the engagement member 155 through tissue structures.

Also shown is connector 160 attached to a passer (not shown) similar to those discussed. The connector 160 may be a threaded rod 162 that is configured to mate with a similarly threaded tube 164 attached to an engagement member 165. As the threaded rod 162 passes through tissue structures and approaches the threaded tube 164, the two may be coupled by screwing the two together and the engagement member 165 is detachably joined to the connector 160. The threaded coupling should be strong enough to maintain the coupling as the passer is withdrawn pulling the engagement member 165 through tissue structures.

An alternate embodiment of an engagement member delivery device 200 is shown in FIGS. 7A-D having an elongate hollow body 201 enclosing an elongate tubular housing 202 that may freely slide along the transverse axis of the body 201. The housing 202 has a guide 204 comprising an elongate flexible curvilinear rod disposed therein. The guide 204 is adapted to assume a generally circular shape when not constrained inside the housing. The guide 204 has a tip 206 configured to penetrate tissue structures of the body. The delivery device 200 further comprises a strap tube 208 and a tubular pusher 210 disposed coaxially about the outside of the housing such that both may slide along the transverse axis of the housing. The strap tube 208 has distal 210 and proximal 211 end portions with the distal end portion configured to couple to a catch 212 located at an opening 214 in the body. The catch is adapted to secure the strap tube to the body 201 as will be shown. The strap tube 208 has an engagement member 216 attached to the proximal end 211.

In use, the body 201 is introduced into the abdomen and the guide 204 is extended from the housing 202 such that the guide makes a generally circular pathway through and around tissue structures 218 and enters the opening 214 in the body 201. The housing 202 is then extended from the body and the strap tube 208 is pushed from the housing along the guide 204 by the pusher 210. The strap tube 208 is pushed through tissue structures 218 while following the guide until it enters the opening 214 and is captured by the catch 212. At this point the strap tube is coupled to the body 201. The guide, pusher and housing are retracted back into the body and the body removed from the abdominal space. As can be seen, as the body is withdrawn, the engagement member 216 is positioned through and around tissue structures 218.

The device of FIGS. 5, 6 and 7 may be positioned and used in such a way that the engagement member 119, 155 or 216 respectively is secured to ventral tissue structures. As shown in FIG. 7E, the engagement members, which may or may not have a leader 220 attached to one end, may be secured to the ventral tissue structures by delivering the engagement member through these tissues in a generally circular pathway shown by arrow 222 with the end of the engagement member protruding through the incision. Again this pathway is generally circular meaning that the pathway is not substantially straight. The engagement member traverses through an arc such that the engagement member may pass into and then through tissue adjacent to the initial placement of the implant and then again exit this same tissue so that an end of the engagement member may be withdrawn with the device and exit at least partially through the incision as shown at least partially in FIG. 11.

As shown in FIGS. 8A-D, the various delivery devices previously described may be made with various shapes and rigidities to facilitate placement of the delivery device in the abdominal space. The delivery device 230 is a generally straight and rigid device with a handle 231 connected at the proximal end. Delivery device 232 has an angular offset bend along its length that may be useful in certain anatomical conditions and delivery device 234 has a general curvilinear shape. Alternatively the delivery device 236 may be flexible and not rigid or may be steerable by the operator.

All the delivery devices previously described may be placed in the abdominal space using positioning aids to guide and direct the placement of the engagement members. These aids may utilize tactile or visual feedback to the operator so that tissue structures such as arteries, veins, nerves, bone, ligaments or tendons in the body can be identified and the placement of the engagement member may be properly directed compared to a blind approach. Referring to FIGS. 9A-C, the delivery device may have a finger loop 250 configured at the distal end such that an operator may place a finger into the loop and utilize tactile feeling in the finger to guide placement of the delivery device end. The finger loop 250 may be attached to the delivery device at point 251 using adhesive or mechanical attachments. The finger loop 250 may also be integrally formed as part of the delivery device. Similarly, the delivery device 252 may have a light source 254 attached to the outer body of the delivery device 252. This light source may be an LED light source and be adapted to radiate a generally confined narrow beam of light. This light may be directed such that the light may be seen through the skin. In this way the operator can utilize the light as a marker to guide positioning as described. In another embodiment the delivery device may be constructed with loops 260 to couple an endoscope 262 to the delivery device. In this way the placement and delivery of engagement members using the delivery device may be controlled through direct visualization by the operator.

Multiple engagement members may be used to secure an implant to the ventral wall. These engagement members may have cords or leaders that extend from the distal ends of the engagement members that may be used to tension the implant. Keeping these ends organized and identified may be challenging. Additionally the sterility of all of these loose ends and the implant must be maintained in a crowded surgical site. To organize and identify the various cords coming from the members, the leaders themselves or the engagement members may be color coded, shape coated or in some other way uniquely identified so that an individual engagement member and its location to the implant and the ventral wall can be determined.

A device to organize the method of implanting the implant and providing a large sterile barrier is illustrated in FIG. 10. A funnel 300 is shown positioned in the incision of a ventral hernia procedure. The hourglass shaped funnel 300 has a wide opening 302 and a narrow opening 304 positioned in the incision and a narrowed neck in between. The funnel may have a straight taper configuration or other configurations as well. The narrow opening 304 may have a retention ring 308 that has an outer diameter greater than the narrow opening 304. The retention ring 308 outer diameter is sized so that once placed into the incision, it retains the funnel 300 in the incision and prevents inadvertent dislodgement of the tunnel from the incision. A drape 310 is attached to the wide opening 302 and extends radially outward from the opening. The drape and funnel may be packaged sterile and the drape is sized to cover an extended surgical area. As can be appreciated when the narrow opening 304 of a sterile funnel is inserted into an incision and the drape extended, an effective sterile barrier is created so that an implant 312 having multiple engagement members 314 may be inserted through the funnel and into the pocket in a sterile, organized manner. Furthermore the engagement members 314 or leaders attached to the ends of the engagement members may be threaded back through the funnel after positioning into a tissue structure. When the end of an engagement member 314 is pulled to apply tension to the implant 312, the inside of the retention ring 304 may act as a fulcrum point and protect the incision edge from abrasion from the member 314. The excess length of the engagement member may be removed, the funnel and drape removed and the incision closed to complete the operation. The excess length may be particularly removed by severing or removing the cord 44 located in a detachment zone 38 as shown in FIG. 2.

In another embodiment of the device and method, after positioning the implant and the engagement members and after the engagement members ends are threaded through the wide opening 302 of the funnel 300, the funnel and drape of FIG. 10 may be removed. The funnel may then be replaced with a small retention tube 320 into which the ends of the engagement members 322 are threaded. The retention tube has a small outside diameter that is sized to allow a smaller incision opening 323 than that required for the funnel. Whereas the funnel opening is larger to accommodate the implant and all of the engagement members, the retention tube is sized to accommodate just the engagement member ends which may be only cords, leaders or sutures. The smaller diameter of the retention tube 320 allows for nearly the complete closure of the incision. The retention tube functions similarly to the funnel because when the end of an engagement member such as member 322 is pulled to apply tension to an implant such as implant 324, the inside of the retention tube may act as a fulcrum point and protect the incision edge from abrasion from the member 322. The excess length of the engagement member 322 may be removed using detachment methods previously described, the retention tube removed and the incision closed to complete the operation.

A tissue structure 340 punctured with an engagement member 342 is shown in FIG. 12. The placement and securement of the engagement member through or around a issue structure 340 may be augmented by directly fastening the engagement member 342 to the tissue structure 340 with the use of staples, clamps, adhesives, sutures or other fastening devices 344. These fasteners 344 insure that the member will not pull out or move relative to the tissue structure. Alternatively the placement and securement of the engagement member 342 through or around tissue structure 340 may be augmented by indirectly fastening the engagement member to the tissue structure with the use of staples, clamps, adhesives, sutures or other fastening devices. In this embodiment the tissue opening around the engagement member 342 is narrowed to pinch the member and further secure the member.

Figures 13A, 13B:
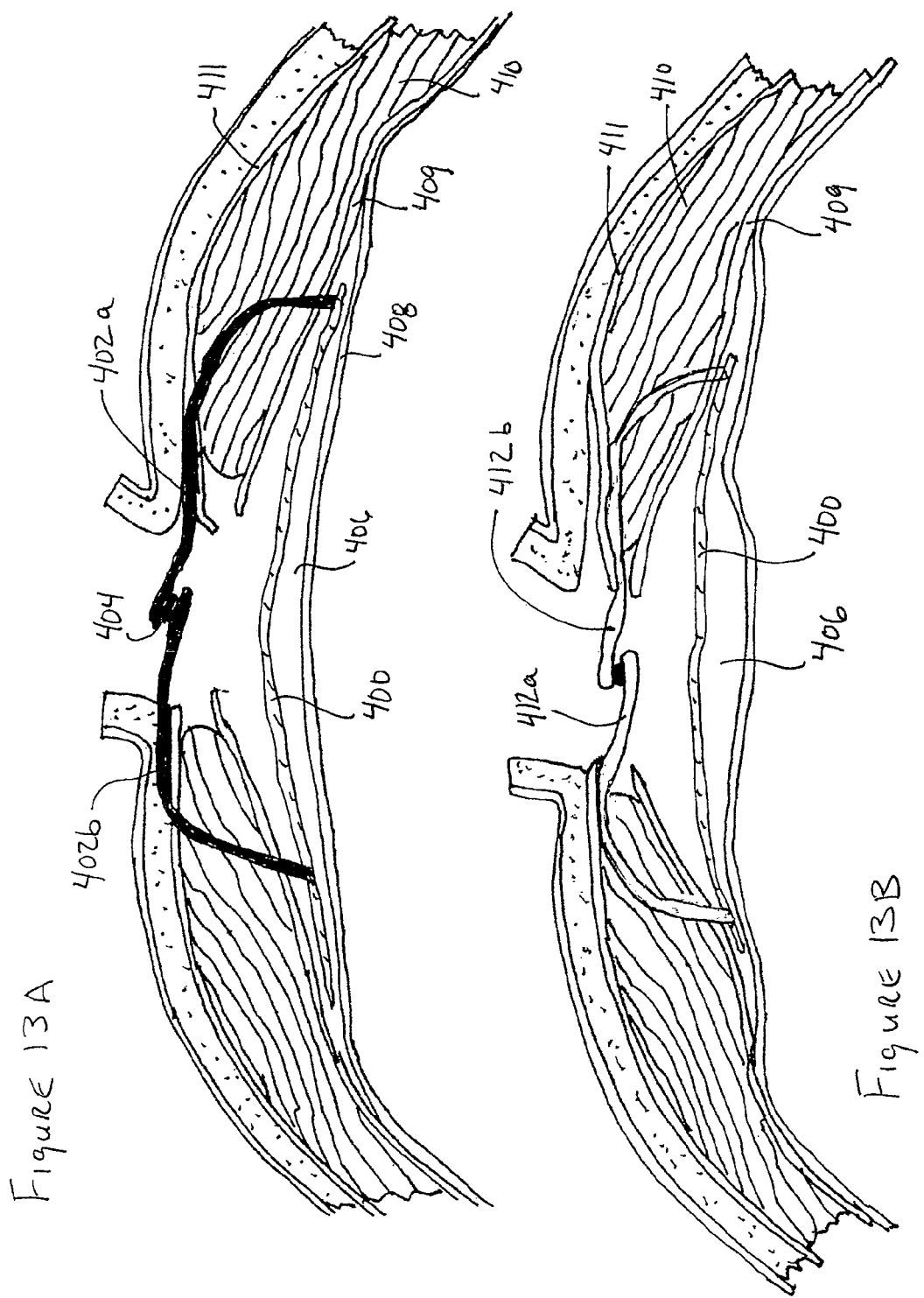
FIG. 13A is a cross-sectional view of an implant positioned in a herniated ventral wall and secured with a set of engagement members connected together between the anterior muscle fascia and the sub dermal layer.
FIG. 13B is a cross-sectional view of an implant positioned in a herniated ventral wall and secured with a set of engagement members connected together between the rectus muscle and the anterior muscle fascia.

An alternative embodiment of the device is an implant and method that are illustrated in FIGS. 13A-B. An incision is made along the midline preferably along a line running from the diaphragm to the pubis and laterally toward the sides of the abdomen. The tissue is dissected down to the level of the peritoneum and an implant 400 is positioned in a pocket 406 formed in a portion of the ventral wall. Preferably this pocket 406 is formed between the peritoneum 408 and the posterior ventral muscle fascia 409 but if no peritoneum is present the implant 400 could be positioned along the posterior ventral muscle fascia 409. The implant 400 is similar to implant 30 and is implanted in a substantially slackened condition relative to the ventral wall as has been previously described. The implant 400 has at least two engagement members 402a-b extending from the implant perimeter and adapted to be inserted through adjoining tissue structures to secure the implant. Specifically the engagement members 402a-b are either pulled or pushed to traverse the posterior ventral muscle fascia 409, the rectus muscle 410 and the anterior ventral muscle fascia 411. The tension and slack of the implant may be adjusted by extending or retracting the engagement members in the tissue structures. The ends of the at least two engagement members are coupled together to secure the implant to the tissue structures described. The engagement members 402a-b may be coupled using suitable fasteners 404 such as suture, mechanical fasteners, hook and loop fasteners otherwise known by the commercial name Velcro®, or adhesives. This list of fasteners is not meant to be limiting and any fastener system commonly known in the art can be used. Any excess length of engagement member may be removed and the incision closed.

In an alternative embodiment of the method, after positioning the implant 400 in the pocket 406, the engagement straps 412a-b are either pulled or pushed to traverse the posterior ventral muscle fascia 409, the rectus muscle 410 and are positioned between the rectus muscle 410 and the anterior ventral muscle fascia 411. The tension and slack of the implant may be adjusted by extending or retracting the engagement members in the tissue structures. The ends of the at least two engagement members are coupled together to secure the implant to the tissue structures described.

Figure 14:
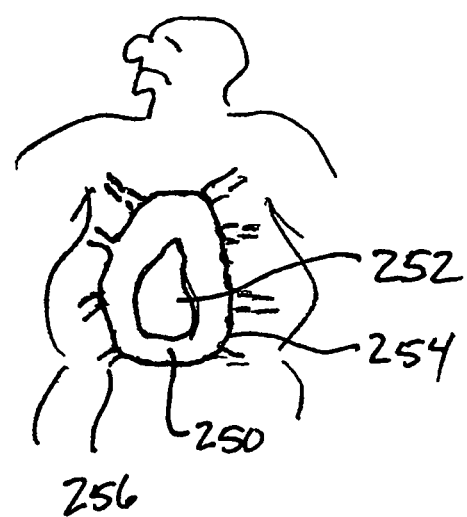
FIG. 14 is a view of an implant template positioned on the skin of a patient over a ventral hernia.

An alternate embodiment of the method of using the implant is shown in FIG. 14. A template 250 may be used before or during the procedure to mark the intended position of the engagement members of the implant. The template 250 is positioned over the incision 252 with the general outline of the template 254 lying on the skin of the patient.

The outline 254 corresponds to the size of the implant. The location of the engagement members 256 are shown by the dotted segments. The operator places the template on the skin of the patient over the hernia and marks the locations of the engagement members on the skin of the patient. After the template is removed, these marks may guide the placement of the engagement members through the ventral wall of the patient.

This invention has been described and specific examples of the invention have been portrayed. The use of those specifics is not intended to limit the invention in anyway. Additionally, to the extent that there are variations of the invention, which are within the spirit of the disclosure or equivalent to the inventions found in the claims, it is our intent that this patent will cover those variations as well.

What is claimed is:

1. A device for securing an engagement member extending from an implant to a ventral wall comprising:
   a passer configured to penetrate at least a portion of the ventral wall in a generally circular path when advanced, said passer having a connector adapted to couple to the engagement member after penetrating the wall, and said passer adapted to pull the engagement member through the path when retracted, a finger ring being located on a distal end segment of the device and configured to at least partially surround a finger of an operator such that tactile feel of the operator can guide the device to an anatomical position.

2. The device of claim 1, wherein the path encircles a tendon, bone, ligament, fascial tissue or muscle portion.

3. The device of claim 1, wherein the passer is made from a super elastic alloy having a pre-set radius, the passer confined by an outer tube and configured such that as the passer is advanced from the tube, the distal end penetrates tissue in a generally circular path.

4. The device of claim 3, wherein the path encircles a tendon, bone, ligament, fascial tissue or muscle portion.

5. The device of claim 1 further comprising a light source attached to the device and configured such that the light penetrates the ventral wall to aid positioning of the device to an anatomical position.

6. A kit for the repair of a ventral wall hernia comprising:
   an implant member and at least a first engagement member defining a first end distanced from the implant member, a second engagement member also extending from the implant and defining a second end distanced from the implant member; and
   a template configured to aid a person in marking an intended position of the engagement members of the implant, the template being positionable on the abdomen of a patient over an actual or intended incision, an outline being on the template and corresponding to the implant, respective locations of the engagement members being indicated on the template, whereby a person can place the template on the patient and mark the respective locations of the engagement members on the skin of the patient such that after the template is removed from the patient, the marks guide placement of the engagement members through the ventral wall of the patient.

7. The kit of claim 6, wherein said kit is adapted to secure the implant to the ventral wall such that when implanted the implant is in a substantially slackened condition relative to the ventral wall.

8. The kit of claim 6, further comprising a retention tube, said tube adapted for placement into the incision after removal of a funnel member and configured to receive leaders connected to an end of the engagement members so that the leaders may be pulled to adjust tension.

* * * * *